(12) United States Patent
Muranushi et al.

(10) Patent No.: US 7,606,609 B2
(45) Date of Patent: Oct. 20, 2009

(54) DEVICES AND METHODS FOR CARDIAC MAPPING OF AN ANNULAR REGION

(75) Inventors: Masamitsu Muranushi, Tokyo (JP); Takashi Higashikubo, Saitama (JP); Pianka Roy, Irvine, CA (US)

(73) Assignee: Irvine Biomedical, Inc., Irvine, CA (US)

( * ) Notice: Subject to any disclaimer, the term of this patent is extended or adjusted under 35 U.S.C. 154(b) by 0 days.

(21) Appl. No.: 12/004,643

(22) Filed: Dec. 21, 2007

(65) Prior Publication Data
US 2009/0163794 A1    Jun. 25, 2009

(51) Int. Cl.
*A61B 5/042* (2006.01)

(52) U.S. Cl. ....................................... 600/374; 600/381
(58) Field of Classification Search ........... 600/374.381
See application file for complete search history.

(56) References Cited

U.S. PATENT DOCUMENTS

| | | | |
|---|---|---|---|
| 5,254,088 A * | 10/1993 | Lundquist et al. | 604/95.04 |
| 5,626,136 A | 5/1997 | Webster, Jr. | |
| 5,779,669 A | 7/1998 | Haissaguerre et al. | |
| 5,860,920 A * | 1/1999 | McGee et al. | 600/374 |
| 5,931,811 A | 8/1999 | Haissaguerre et al. | |
| 5,951,471 A | 9/1999 | de la Rama et al. | |
| 6,002,955 A * | 12/1999 | Willems et al. | 600/374 |
| 6,308,090 B1 | 10/2001 | Tu et al. | |
| 6,322,524 B1 | 11/2001 | Kensey et al. | |
| 6,356,790 B1 * | 3/2002 | Maguire et al. | 607/102 |
| 6,628,976 B1 | 9/2003 | Fuimaono et al. | |
| 6,711,428 B2 | 3/2004 | Fuimaono et al. | |
| 7,013,170 B2 * | 3/2006 | Bowe | 600/374 |

* cited by examiner

*Primary Examiner*—Lee S Cohen

(57) ABSTRACT

A catheter maps an electrical conduction pattern in an annular region of a heart. The catheter has a tubular shaft that has a pre-shaped curved distal section adjacent the distal end thereof, and at least one lumen extending between the distal end and the proximal end of the shaft, with a plurality of electrodes disposed on the distal section. A handle is attached to the proximal end of the shaft, with a steering mechanism provided at the handle for adjusting the curvature of the distal section, and a deflection mechanism provided at the handle for deflecting the distal section. The electrodes are positioned in a parallel plane separate from the shaft when the distal section is undeflected.

15 Claims, 9 Drawing Sheets

SECTION A-A

SECTION B-B

DEVICES AND METHODS FOR CARDIAC MAPPING OF AN ANNULAR REGION

BACKGROUND OF THE INVENTION

1. Field of the Invention

The present invention generally relates to a medical device and its use for mapping electrical activity inside the heart especially in the tricuspid valve.

2. Description of the Prior Art

Symptoms of abnormal heart rhythms are generally referred to as cardiac arrhythmias, while an abnormally rapid rhythm is referred to as a tachycardia. The present invention is concerned with the diagnosis and treatment of tachycardias, which are frequently caused by the presence of an "arrhythmogenic region" or an "accessory atrioventricular pathway" close to the inner surface of the atrium of a heart. The heart includes a number of normal pathways, which are responsible for the propagation of electrical signals from the upper chamber to the lower chamber, and which are necessary for performing normal systole and diastole function. The presence of an arrhythmogenic region or an accessory pathway in the atria can bypass or short circuit the normal pathway, potentially resulting in very rapid heart contractions, referred to here as atrial flutter. Atrial flutter is generally characterized by a saw tooth pattern with negative deflections in inferior leads of the ECG, while the atrial rate is in the range of 240-340 beats per minute.

Treatment of atrial flutter may be accomplished by a variety of approaches, including drugs, surgery, implantable pacemakers/defibrillators, and catheter ablation. While drugs may be the choice of treatment for many patients, they only mask the symptoms and do not cure the underlying causes, and they may also cause side effects. Implantable devices only correct the arrhythmia after it occurs. Surgical and catheter-based treatments, on the other hand, will actually cure the problem, usually by ablating the abnormal arrhythmogenic tissues or the accessory pathways responsible for the tachycardia.

There are, however, several drawbacks of the currently-available mapping catheters when used in locating areas of aberrant electrical conduction for the catheter-based ablation of an annular region of the heart such as the tricuspid valve. Due to the varying anatomy of this area between different patients, one of the major problems lies in the unstable positioning of the catheter electrodes around the triscuspid valve annulus. When a catheter is not stabilized, the electrodes cannot maintain sufficient contact with the target tissue and hence the heart's electrical conduction pattern becomes difficult to map and establish. Furthermore, many of these currently-available catheters lack a soft distal tip portion so that the shock from contacting the catheter tip on the tissue can be absorbed.

Therefore there is a need for an improved catheter that can used in the mapping of a tricuspid valve as a diagnostic device to aid in the treatment of atrial flutter.

SUMMARY OF THE DISCLOSURE

It is an object of the present invention to provide a catheter and a catheter-based method for use in mapping and pacing in the tricuspid valve region.

It is another object of the present invention to provide a method for mapping and pacing of the tricuspid valve using a catheter that has a soft distal tip section so that the catheter tip moves and rebounds longitudinally.

The objectives of the present invention are accomplished by providing a catheter for mapping an electrical conduction pattern in an annular region of a heart. The catheter has a tubular shaft that has a pre-shaped curved distal section adjacent the distal end thereof, and at least one lumen extending between the distal end and the proximal end of the shaft, with a plurality of electrodes disposed on the distal section. A handle is attached to the proximal end of the shaft, with a steering mechanism provided at the handle for adjusting the curvature of the distal section, and a deflection mechanism provided at the handle for deflecting the distal section. The electrodes are positioned in a parallel plane separate from the shaft when the distal section is undeflected.

DETAILED DESCRIPTION OF THE PREFERRED EMBODIMENTS

Figure 1:
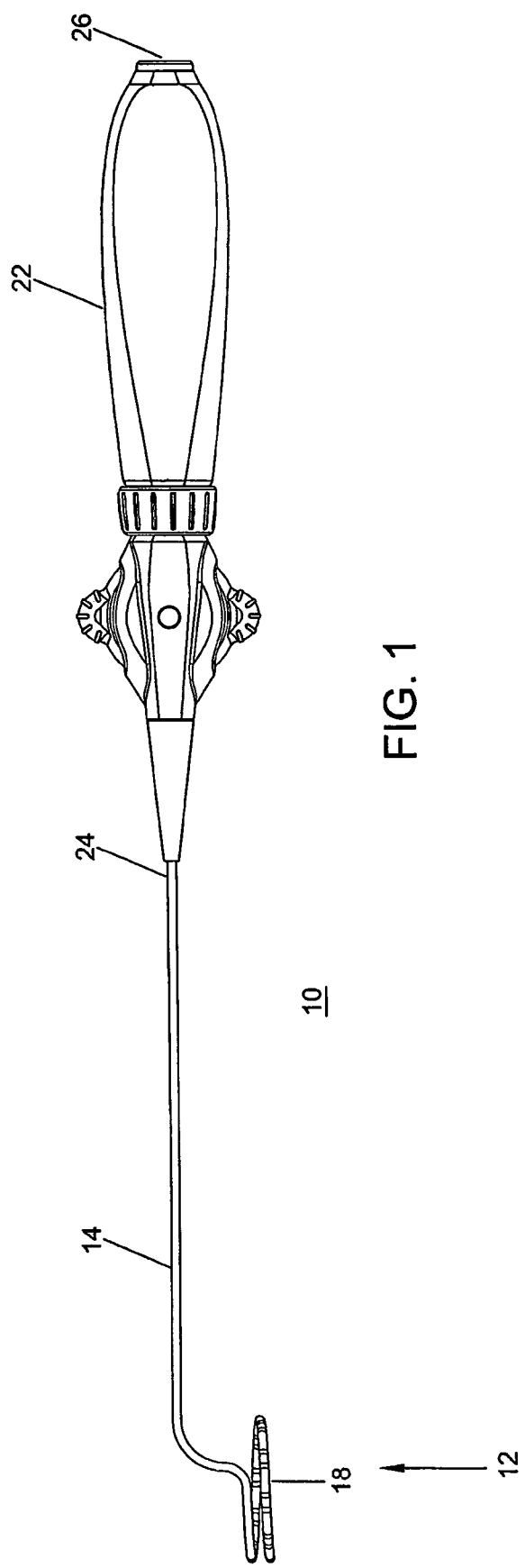
FIG. 1 is an overall view of a catheter system according to one embodiment of the present invention, shown in a non-actuated position.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices and mechanisms are omitted so as to not obscure the description of the present invention with unnecessary detail.

FIGS. 1-7 illustrate a catheter 10 having a catheter body 14 that comprises an elongated tubular construction having a single, axial or central lumen 20. The catheter body 14 is flexible, i.e., bendable, but substantially non-compressible along its length. The catheter body 14 can be of any suitable construction and made of any suitable material. A presently preferred construction comprises an outer wall made of polyurethane or PEBAX. The outer wall can comprise an imbedded braided mesh of stainless steel or the like to increase torsional stiffness of the catheter body 14 so that when the control handle 22 is manipulated, the intermediate section of the catheter 10 will rotate in a corresponding manner. The outer diameter of the catheter body 14 is not critical, but is preferably no more than about 8 French, more preferably 6 or 7 French. Likewise the thickness of the outer wall is not critical, but is thin enough so that the central lumen 20 can accommodate wires, cables or tubes (as described below). If desired, the inner surface of the outer wall can be lined with a stiffening tube (not shown) to provide improved torsional stability.

Figure 6:
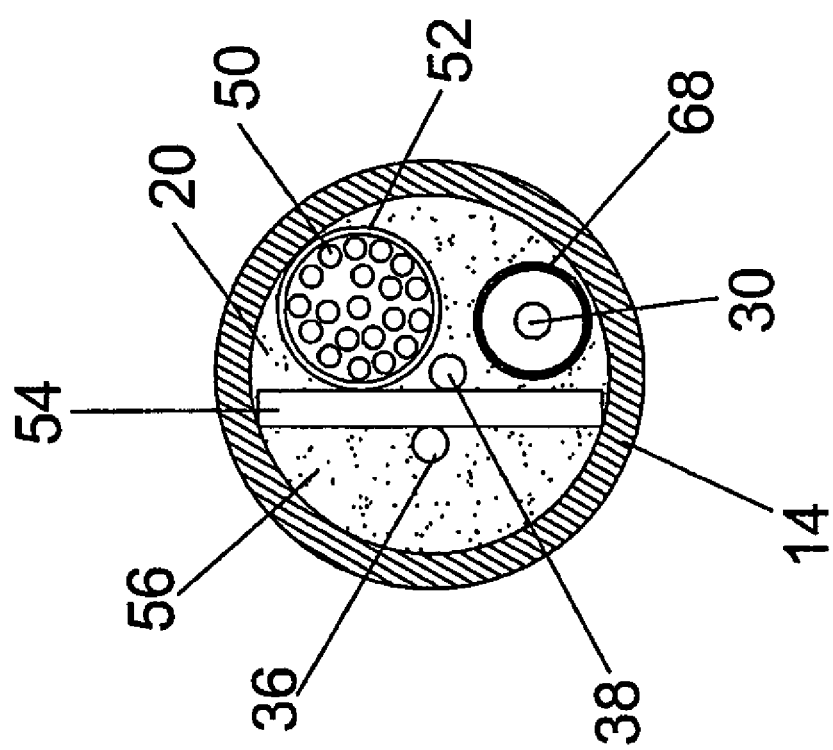
FIG. 6 is a cross-sectional view of the catheter system taken along the lines A-A in FIG. 4.

The central lumen 20 extends through the catheter body 14 (see FIG. 6). A control handle 22 is attached to the proximal end 24 of the catheter body 14. A connector 26 is secured at the proximal end of the handle 22. A pre-shaped distal section 12 is provided adjacent the distal end 16 of the catheter body 14. A series of ring electrodes 18 are mounted on the non-conductive covering of the generally circular distal section 12. The ring electrodes 18 can be made of any suitable solid conductive material, and can be formed of conducting materials selected from the group consisting of platinum, iridium, gold, silver, stainless steel, Nitinol, tungsten, or an alloy of their mixture. The electrodes 18 can be mounted onto the non-conductive covering with glue or the like. Alternatively, the ring electrodes 18 can be formed by coating the non-conductive covering with an electrically conducting material, like platinum, gold and/or iridium. The coating can be applied using sputtering, ion beam deposition or an equivalent technique.

Figure 4:
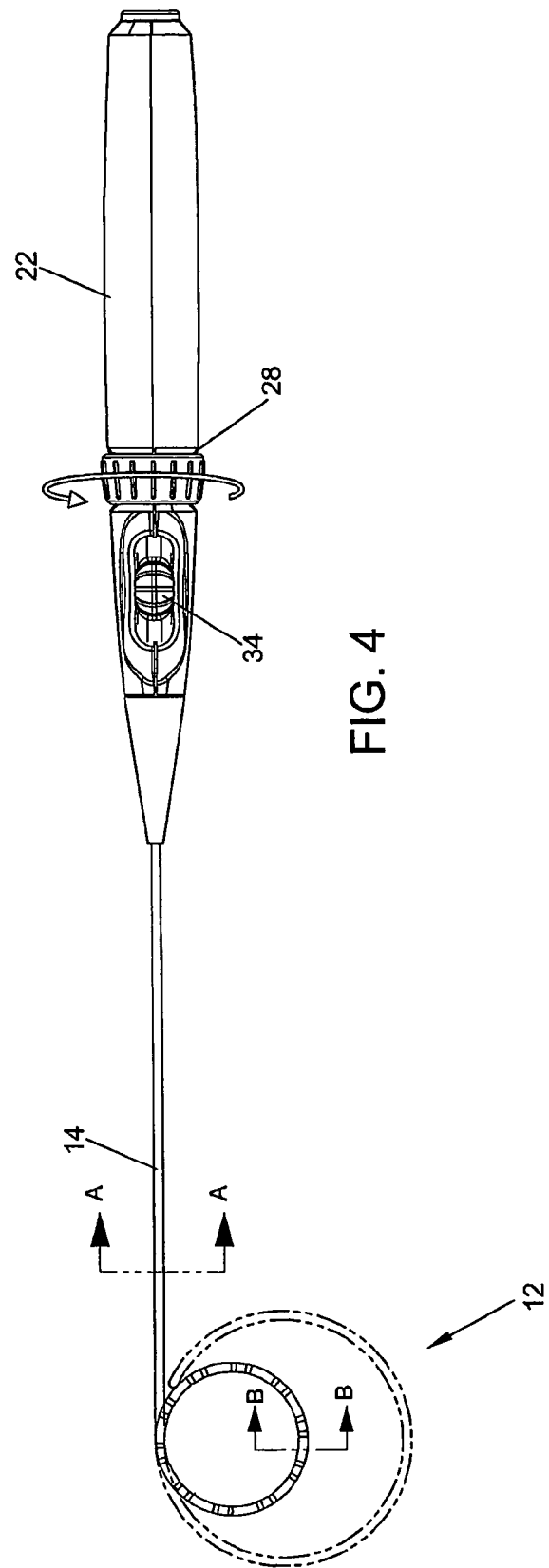
FIG. 4 illustrates the catheter system of FIG. 1 with the distal section manipulated for mapping.

As shown in FIG. 4, a steering mechanism 28 is provided on the handle 22 to vary the diameter of the generally circular distal section 12 of the catheter body 14 for catheter maneuvering and positioning in and around the tricuspid valve region of the heart. The steering mechanism 28 can be implemented in the form of a rotary wheel that is coupled to a puller wire 30 (see FIG. 6) that is in turn coupled to the distal end 16 to change the diameter of the distal section 12. The puller wire 30 extends through the distal section 12 (see FIG. 7) as well. By manipulating (turning) the steering mechanism 28 in either direction, the distal section 12 changes its diameter as shown in FIG. 4. The puller wire 30 is made of any suitable metal, such as stainless steel or Nitinol, and is preferably coated with polyimide, TEFLON™ or the like. The coating imparts lubricity to the puller wire 30. Referring to FIG. 6, a short compression coil 68 is situated towards and inside the distal end of the catheter body 14 to stabilize the catheter shaft when the puller wire 30 is activated by the steering mechanism 28. The compression coil 68 is made of any suitable metal, preferably stainless steel. The compression coil 68 is tightly wound on itself to provide flexibility for bending. The inner diameter of the compression coil 68 is preferably slightly larger than the diameter of the puller wire 30. The TEFLON™ coating on the puller wire 30 allows it to slide freely within the compression coil 68. Longitudinal movement of the puller wire 30 relative to the catheter body 14, which results in deflection of the distal section 12, is accomplished by suitable manipulation of the steering mechanism 28. Examples of suitable control handles that can be used for the present invention are disclosed, for example, in U.S. Pat. Nos. Re 34,502 and 5,897,529, the entire disclosures of which are incorporated herein by reference.

Figure 2:
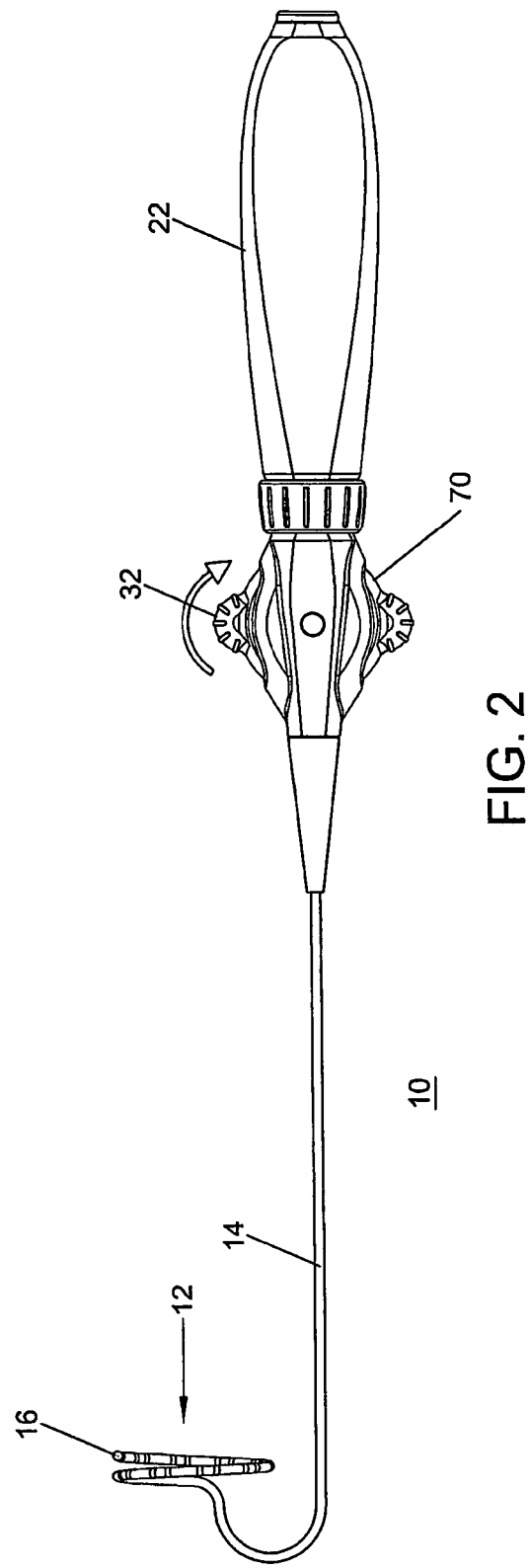
FIG. 2 illustrates the catheter system of FIG. 1 with the distal section deflected to one side.
Figure 3:
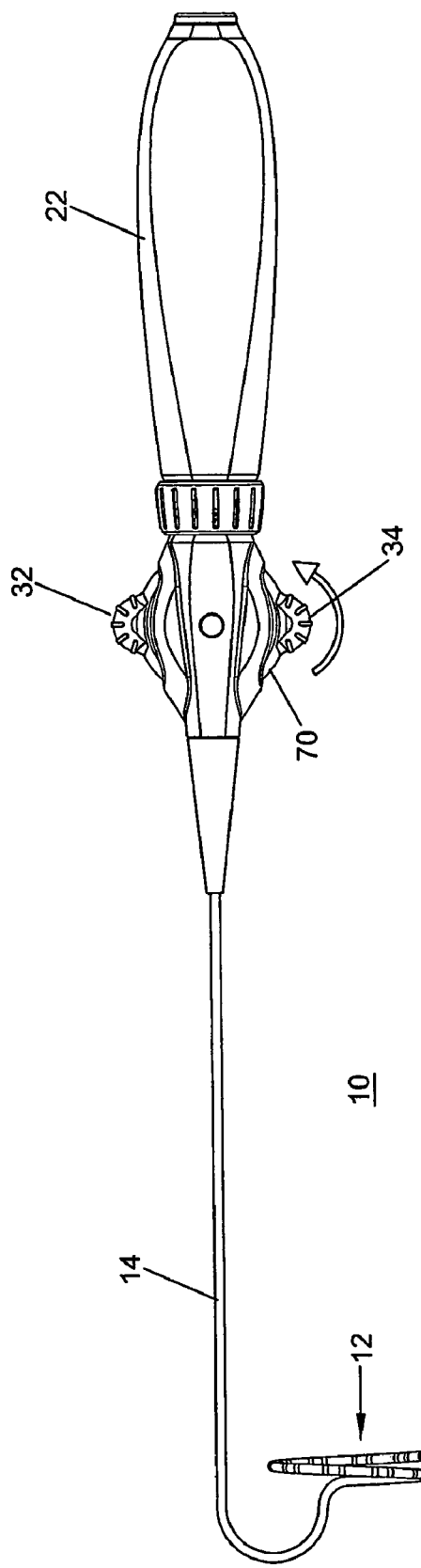
FIG. 3 illustrates the catheter system of FIG. 1 with the distal section deflected to another side.

As shown in FIGS. 2 and 3, actuator grips 32 and 34 are coupled to a steering wheel 70 of the handle 22 for deflecting the distal section 12. The actuator grips 32, 34 can be extensions located on opposite sides of the steering wheel 70 coupled to separate activation wires 36 and 38, respectively (see FIG. 6). The activation wires 36, 38 terminate in the catheter body 14 before the distal section 12. When the steering wheel 70 is turned in one direction, the distal section 12 deflects to one side (see FIG. 2), and when the steering wheel 70 is turned in the other direction, the distal section 12 deflects to the other side (see FIG. 3).

Figure 5:
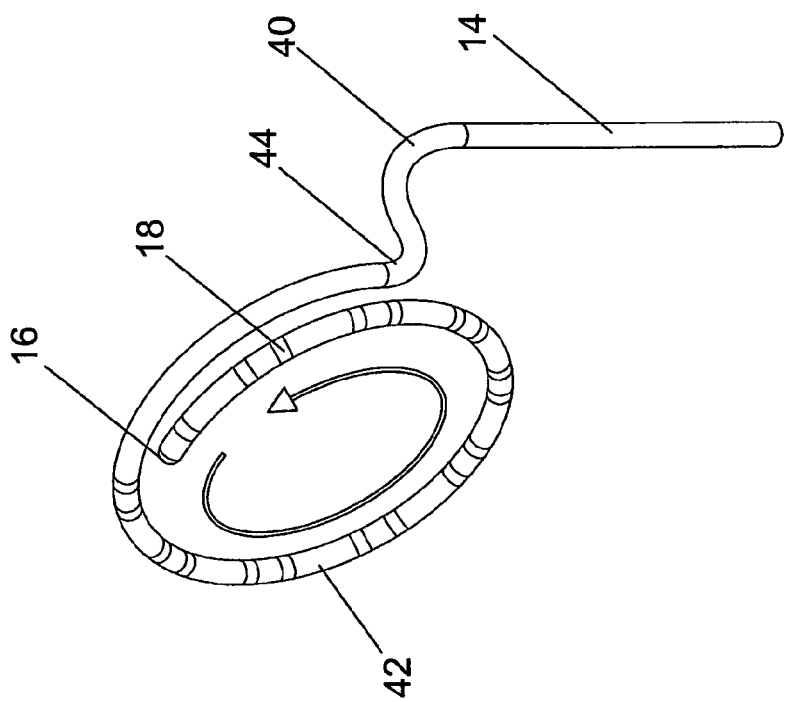
FIG. 5 is a perspective view of the distal section of the catheter system of FIG.

FIG. 5 shows a close-up view of the distal section 12, which has one generally circular section in a plane parallel to the catheter body 14 and a second section that has two alternating angles. The circular section is a pre-shaped curve 42, and the second section with two alternating angles is a pre-shaped transitional section 40. The distal section 12 functions to allow the plurality of electrodes 18 to be positioned at the tricuspid valve annulus. The transitional section 40 which extends from the catheter body 14 forms a curve or bend that is about ninety degrees from the plane defined by the catheter body 14. From the distal end 44 of the transitional region 40, the curve 42 is generally circular and extends in a helical manner until it terminates at the distal end 16. The length of the distal section 12 (from the distal end 44 of the transitional region 40 to the distal end 16 of the catheter 10) ranges from 7 to 15 cm, with the curve 42 having an outer diameter preferably ranging from about 40 mm to about 50 mm. The regions between the distal ends 44 and 16 and the transitional region 40 are specifically designed for the purpose of positioning and stabilizing the electrodes 18 in the target area within the heart during electrophysiology study.

When introducing the catheter 10 into the right atrium, the steering wheel 70 is manipulated so that the distal section 12 of the catheter body 14 can be deflected to adjust to the angle of the patient's tricuspid valve. When the catheter 10 is located in the target area, the steering mechanism 28 can be manipulated so that the diameter of the distal section 12 can be varied to fit the size of the patient's tricuspid valve.

Figure 7:
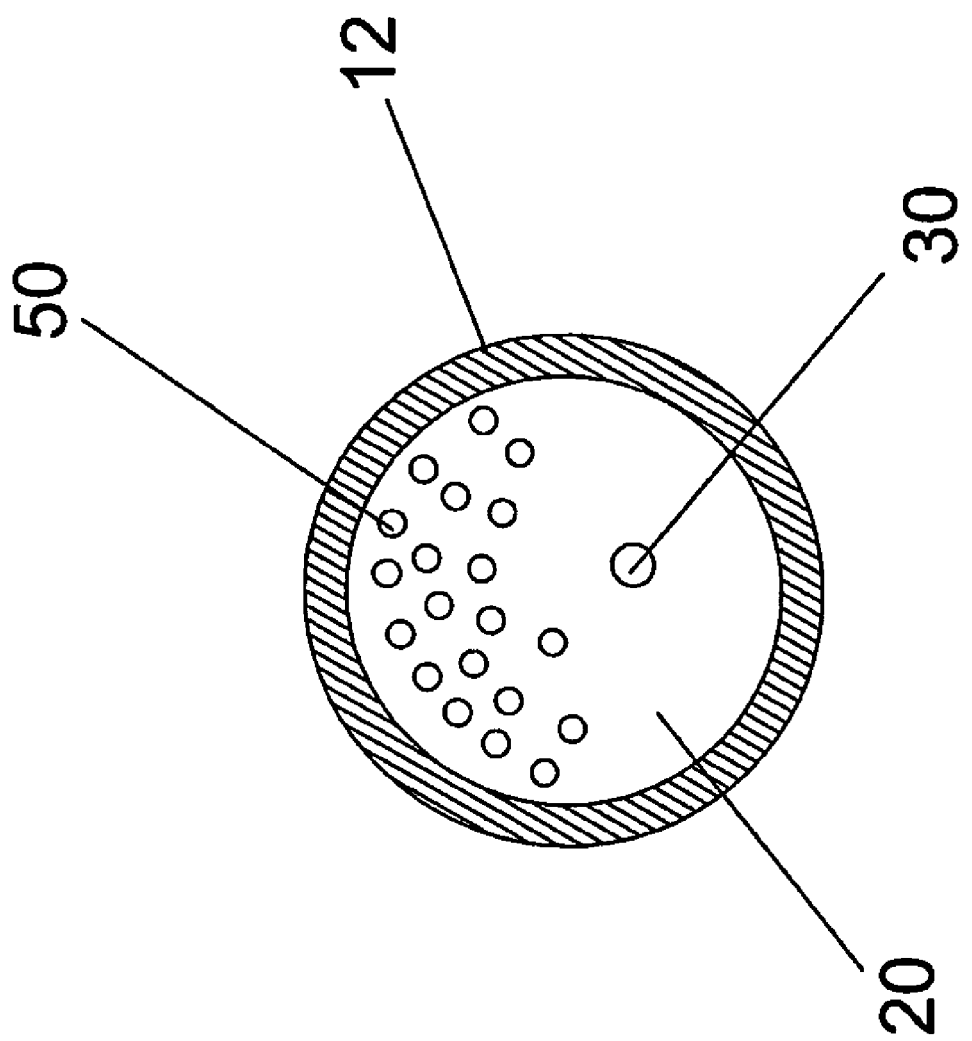
FIG. 7 is a cross-sectional view of the catheter system taken along the lines B-B in FIG. 4.

Referring now to FIGS. 5-7, a plurality of electrodes 18 is disposed on the distal section 12. Conducting wires 50 are connected to respective electrodes 18 for transmitting the intracardiac signal from each electrode 18 to an external EP monitor. The conducting wires 50 can be housed inside a protective polyimide tubing 52. The activation wires 36 and 38 can be secured to a flat wire 54. The activation wires 36 and 38 are activated to cause the flat wire 54 to bend, and thereby bend the distal section 12 of the catheter body 14. The flat wire 54, the wires 30, 36, 38, the coil 68, and the tubing 52 (and its enclosed conducting wires 50) are all housed inside the lumen 20. Adhesive 56 can be provided inside the lumen 20 in a manner to secure all of these components at fixed locations within the lumen 20 while still allowing the activation wires 36 and 38 to move up and down within the lumen 20 when activated by the steering wheel 70.

Figure 8:
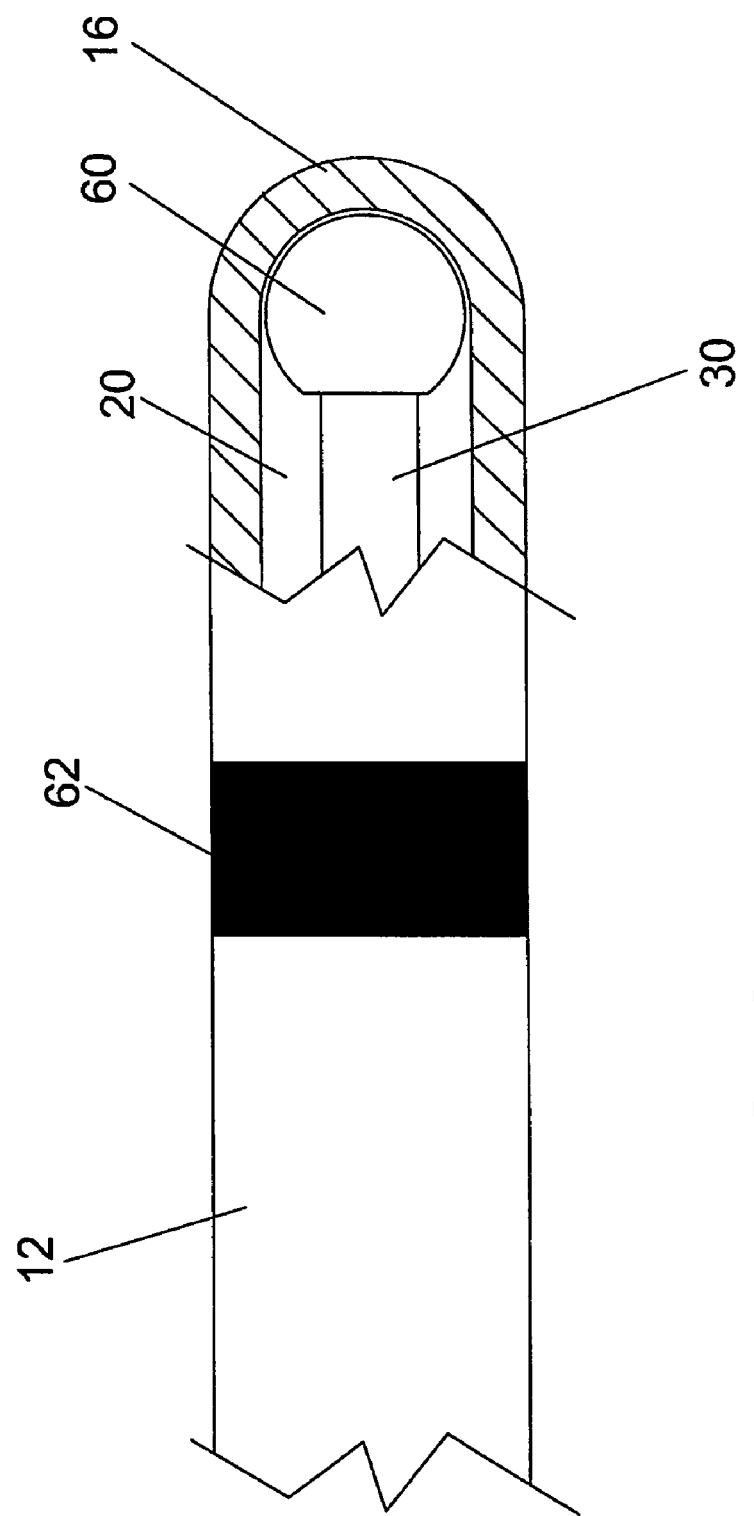
FIG. 8 is a longitudinal cross-sectional view of the distal section of the catheter system of FIG. 1.

FIG. 8 illustrates the distal end 16 of the catheter 10 at the distal section 12, which has an atraumatic design to prevent the distal end 16 of the catheter 10 from penetrating tissue. The puller wire 30 terminates at a bulbous tip 60 which can either be provided in one piece with the puller wire 30, or be provided as a separate bulbous tip that is secured to the distal tip of the puller wire 30. The bulbous tip 60 can be made of metal or plastic material, preferably stainless steel, Nitinol, or PEEK. The distal end 16 is formed preferably by heating to enclose the bulbous tip 60 within the catheter shaft material, which is preferably Pebax or polyurethane. A ring electrode 62 is attached to the distal end 16 for recording intracardiac signals.

Figure 9:
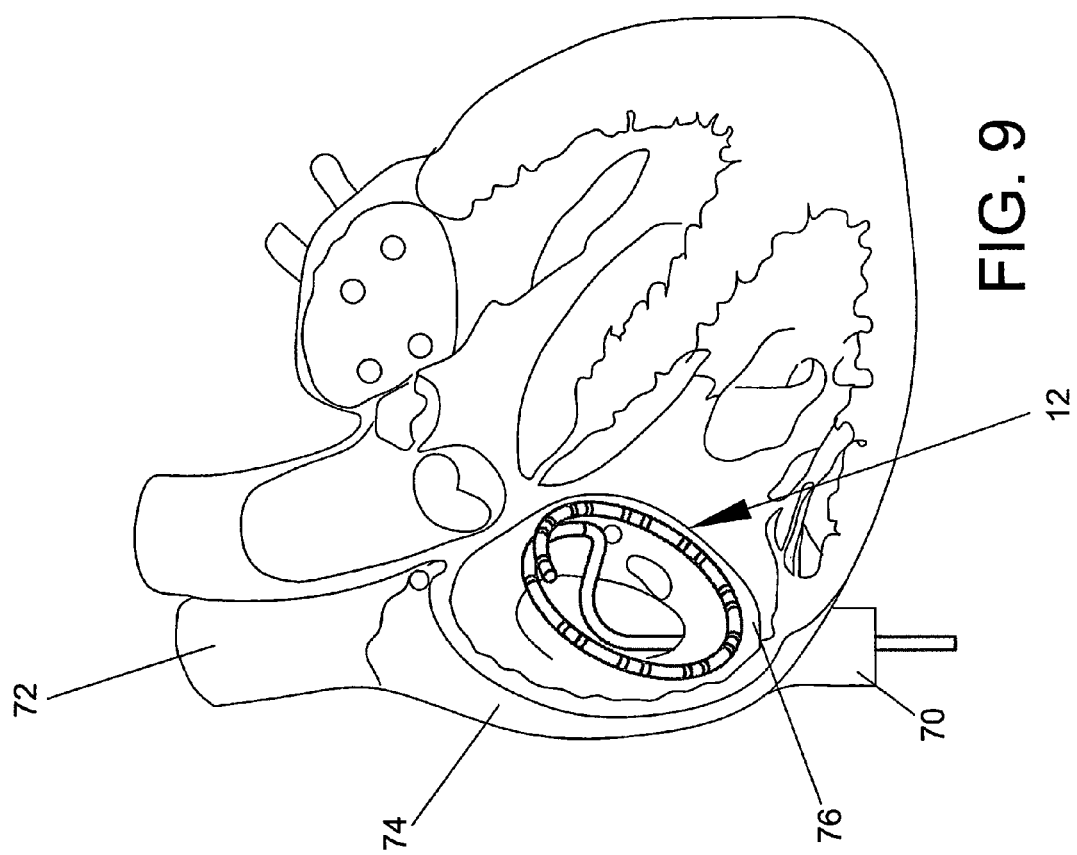
FIG. 9 illustrates the operation of the catheter system of FIG. 1.

FIG. 9 illustrates one of the methods of use of the present invention for illustration purposes. Blood flows from both the inferior vena cava 70 and/or the superior vena cava 72 to the right atrium 74 of the heart. The right atrium 74 is separated by a tricuspid valve 76 from the right ventricle. The catheter 10 is inserted into the right atrium 74 of the heart, and the distal section 12 is deflected inside the right atrium 74, with the transitional section 40 used as anchoring points of stabilizing the distal section 12 to position the distal section 12 in the tricuspid valve 76. The actuator grips 32 and 34 are engaged to turn the steering wheel 70 to deflect the distal section 12 of the catheter body 14 to properly position the distal section 12 with the anatomical angle of the patient's tricuspid valve. Then the steering mechanism 28 is manipulated to adjust the diameter of the curve 42 of the distal section 12 to properly position plurality of electrodes 18 around the tricuspid valve annulus region. The electrical conductance pattern is established by mapping the endocardial surface, including the tricuspid valve annulus and within the coronary sinus, where the mapped electrical conduction pattern is used to assist in locating areas of aberrant electrical conduction, and to assist in the ablation of atrial flutter indications.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A catheter for mapping an electrical conduction pattern in a tricuspid valve region of a heart, comprising:
   a tubular shaft having
      a distal end and a proximal end,
      a pre-shaped distal section adjacent the distal end, the pre-shaped distal section adapted to conform to a tricuspid valve region of a heart and having a first generally circular section and a second transitional section having two alternating angles located proximal the first generally circular section, at least one lumen extending between the distal end and the proximal end, and a plurality of electrodes disposed along the first generally circular section;
   a handle attached to the proximal end of the shaft;
   a steering mechanism provided within the handle for varying a diameter of the first generally circular section; and
   a deflection mechanism provided within the handle for deflecting the distal section bi-directionally;
wherein the electrodes are positioned in a plane parallel to the shaft when the distal section is undeflected.

2. The catheter of claim 1, further including a puller wire coupled to the steering mechanism, the puller wire extending through the lumen into the distal section, and including a bulbous tip provided at a distal end of the puller wire.

3. The catheter of claim 2, further comprising a short compression coil surrounding a portion of the puller wire near the distal end of the shaft.

4. The catheter of claim 1, wherein the first generally circular section comprises a bulbous tip within the shaft adjacent the distal end to prevent the distal end from puncturing tissue.

5. The catheter of claim 1, further comprising
   a flat wire; and
   a first activation wire and a second activation wire, each of the first and the second activation wires coupled to the flat wire along their length, wherein the flat wire, the first activation wire and the second activation wire extend from the proximal end of the tubular shaft to a location just proximal of the second transitional section.

6. The catheter of claim 5, wherein the first activation wire and the second activation wire are disposed on opposite sides of the flat wire.

7. The catheter of claim 5, further comprising a puller wire coupled to the steering mechanism and extending through the lumen into the distal section.

8. The catheter of claim 7, further comprising a bulbous tip at a distal end of the puller wire.

9. The catheter of claim 7, further comprising an adhesive within the lumen to maintain the puller wire and the flat wire in fixed positions relative to each other, and wherein the puller wire may be manipulated longitudinally.

10. The catheter of claim 7, further comprising a short compression coil surrounding a portion of the puller wire near the distal end of the shaft.

11. The catheter of claim 5, further comprising a first actuator grip coupled to the first activation wire, a second actuator grip coupled to the second activation wire, and a steering wheel,
   wherein the first actuator grip and the second actuator grip are coupled to opposite sides of the steering wheel.

12. The catheter of claim 1, wherein the two alternating angles are each about 90 degrees.

13. A method for mapping an electrical conduction pattern of a tricuspid valve region of a heart comprising the steps of:
   a) inserting a catheter into a right atrium of the heart, the catheter having a tubular shaft having a distal end and a proximal end, a pre-shaped distal section adjacent the distal end, the pre-shaped distal section adapted to conform to a tricuspid valve region of a heart and having a first generally circular section and a second transitional section located proximal the first generally circular section and having two alternating angles, at least one lumen extending between the distal end and the proximal end, and a plurality of electrodes disposed along the first generally circular section, the catheter further including a handle attached to the proximal end of the shaft, the handle having a steering mechanism for varying a diameter of the first generally circular section, and a deflection mechanism for deflecting the distal section bi-directionally, wherein the electrodes are positioned in a plane parallel to the shaft when the distal section is undeflected;
   b) deflecting the distal section inside the right atrium to position the distal section onto the tricuspid valve region, wherein the second transitional section is used as an anchoring point for stabilizing the distal section of the catheter shaft inside the right atrium;
   c) exposing the plurality of electrodes to an endocardial tissue around the tricuspid valve region;
   d) steering the distal end of the catheter to vary the diameter of the first generally circular section and conform the first generally circular section to the size of the tricuspid valve region; and
   e) mapping the surface of the endocardial tissue, including the tricuspid valve region, wherein the electrical conduction pattern is used to assist in locating areas of aberrant electrical conduction.

14. The method of claim 13, wherein
   the catheter further comprises a puller wire coupled to the steering mechanism and extending through the lumen to the distal end of the catheter and a flat wire coupled to the deflection mechanism and extending through the lumen to a location proximal of the second transitional section,
   wherein the lumen further comprises an adhesive to maintain the puller wire and the flat wire in laterally fixed positions relative to spacing from the interior of the lumen, and
   wherein the steering step comprises manipulating the steering mechanism to move the puller wire longitudinally within the lumen.

15. The method of claim 14, wherein
   the catheter further comprises a first activation wire and a second activation wire coupled to the flat wire, and
   wherein the deflecting step comprises manipulating the deflection mechanism to move at least one of the first and the second activation wires longitudinally within the lumen.

* * * * *